United States Patent [19]

Manning et al.

[11] Patent Number: 5,514,560
[45] Date of Patent: May 7, 1996

[54] SUBSTRATES FOR βGALACTOSIDASE

[75] Inventors: Wayne B. Manning, Antioch; Pyare Khanna, Fremont; Glenda Choate, Pleasant Hill, all of Calif.

[73] Assignee: Boehringer Mannheim Corporation, Indianapolis, Ind.

[21] Appl. No.: 453,904

[22] Filed: May 30, 1995

Related U.S. Application Data

[62] Division of Ser. No. 394,495, Aug. 16, 1989, Pat. No. 5,444,161.

[51] Int. Cl.$^6$ .......................... C12Q 1/54; G01N 33/573
[52] U.S. Cl. ................................ 435/14; 435/7.4
[58] Field of Search .................. 435/4, 7.4, 14, 435/7.1

[56] References Cited

U.S. PATENT DOCUMENTS

| | | | |
|---|---|---|---|
| 3,427,380 | 2/1969 | Sarett et al. | 536/17.4 |
| 3,547,902 | 12/1970 | Schmitz et al. | 536/17.4 |
| 4,668,622 | 12/1986 | Kuhr et al. | 435/14 |
| 4,708,924 | 11/1987 | Henderson | 435/7 |
| 4,952,495 | 8/1990 | Belly et al. | 435/18 |

*Primary Examiner*—John W. Rollins
*Attorney, Agent, or Firm*—Luann Cserr

[57] ABSTRACT

Galactopyranoside derivative compounds for use as substrates for hydrolysis by enzymes with β-galactosidase activity are provided. The concentration of the reaction products can be measured by spectroscopy. The compounds find particular use in diagnostic assays for detection of analyte.

6 Claims, No Drawings

SUBSTRATES FOR β GALACTOSIDASE

CROSS REFERENCE TO RELATED APPLICATIONS

This application is a divisional of U.S. application Ser. No. 07/394,495, filed Aug. 16, 1989, now U.S. Pat. No. 5,444,161.

TECHNICAL FIELD

The present application relates to substrates for β-galactosidase, their preparation, and their use in assays.

1. Background

The enzyme β-galactosidase, and its derivatives, are used in innumerable assays. β-galactosidase is able to hydrolyze multiple substrates. The choice of substrate for an assay involving an enzyme with β-galactosidase activity (EC 3.2.1.23) is contingent upon the conditions under which the enzymatic reaction takes place and the conditions under which the concentration of reaction products must be determined. Some of the more important factors to consider when selecting a substrate for a given assay include solubility, stability, affinity for the enzyme, speed of the reaction, strength of the signal generated, and the absorbance wavelength at which the assay results are determined. As the variety of assays that involve measuring β-galactosidase activity increases, the need for more substrates with different properties will also increase because the constraints placed upon the substrates will also increase.

2. Relevant Literature

U.S. Pat. No. 4,708,929 teaches the use of ED and EA to measure the concentration of analyte in CEDIA™ assays. This patent is herein incorporated by reference.

European patent application EP-A-0 292 169 discloses new substrates capable of being hydrolyzed by β-galactosidase. Other β-galactosidase subtrates are described in *Analyt. Chimica Acta* (1984) 163:67–72; Stokes and Wilson, *Biochemistry* (1972) 11:1061–1064: and European Patent Application EP-A-0-146-866.

SUMMARY OF THE INVENTION

New substrates for enzymes with β-galactosidase activity are given. These substrates are β-D-galactopyranoside conjugates to nitrophenyl derivatives. These substrates possess physical, chemical, and enzymatic substrate properties that make them superior to conventional β-galactosidase substrates, such as ONPG (o-nitrophenyl-β-D-galactopyranoside).

DESCRIPTION OF SPECIFIC EMBODIMENTS

The present invention provides novel substrates for hydrolysis by enzymes with β-galactosidase activity. The subject substrates may be employed in procedures where they possess significant advantages over conventional β-galactosidase substrates.

The compounds provided for are of the formula:

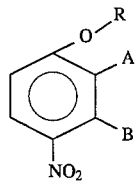
(I)

wherein either A or B, but not both is hydrogen, and when other than hydrogen, A is methoxyl (—OCH$_3$) or formyl (—CHO), and B is —NO$_2$ or —CN. R is a β-D-galactosidyl moiety.

Specifically, the synthesis and properties of four compounds of formulae (I) are described in this application. The chemical names of these compounds are as follows:

o-Methoxy-p-nitrophenyl-β-D-galactopyranoside (NGPG), is of formula (I) wherein A is —OCH$_3$;

3,4-Dinitrophenyl-β-D-galactopyranoside (3,4 DNPG), is of formula (I), wherein B is —NO$_2$;

m-Cyano-p-nitrophenyl-β-D-galactopyranoside (m—CN—NPG), is of formula (I), wherein B is —CN; and, 4-Nitrosalicylaldehyde-β-D-galactopyranoside (NSPG), is of formula (I), wherein A is —CHO.

Enzymes with β-galactosidase activity act on the subject compounds by hydrolyzing the bond between the C$_1$ of the galactopyranoside moiety and the adjacent oxygen. The concentration of nitrophenyl derivative liberated by the enzymatic reaction is readily measured by spectroscopy.

The subject compounds may be used as substrates for a variety of enzymes with β-galactosidase activity. These enzymes may be β-galactosidase itself, β-galactosidase fusion proteins, or complexes of fragments or modified fragments of β-galactosidase. Of particular interest is when the subject substrates are hydrolyzed by a complex of two peptides derived from β-galactosidase, wherein the peptides consists of an α-complementation fragment (or a derivative wherein the α-complementation fragment is conjugated to an analyte to be measured) and an α complementation acceptor. This complex of two β-galactosidase derived peptides will usually be EA and ED derivatives as described in U.S. Pat. No. 4,708,929.

The substrates described in this application may be employed in procedures that call for the measurement of β-galactosidase activity. For example, β-galactosidase and its derivatives find numerous uses throughout molecular biology. β-galactosidase is commonly used to measure the expression of genes that are difficult to assay by conventional means, by fusion of the β-galactosidase gene to the gene of interest.

β-galactosidase-analyte conjugates may be used in a variety of diagnostic assays. The subject compounds may be used in conjunction with these assays. Such assays may be used to determine the presence and/or concentration of various compounds, including specific proteins, carbohydrates, and polynucleotides. The assays may be heterogenous, including ELISA assays. In particular the subject compounds may be employed in CEDIA™ assays. CEDIA™ assays measure the amount of an analyte by means of the ability of the analyte to affect the observed enzyme activity when employing an anti-analyte antibody binding reaction to a β-galactosidase α complementing fragment conjugated to analyte or cross reactive compound. In the absence of free analyte, the observed β-galactosidase activity is lower. Thus in CEDIA™ assays β-galactosidase activity increases as the amount of analyte increases. CEDIA™ assays make use of the α complementation phenomenon between ED and EA as described in detail in U.S. Pat. No. 4,708,929.

The choice of an appropriate substrate for a procedure involving the measurement of β-galactosidase activity is dependent upon several factors such as the required sensitivity of the assay, the required speed of the assay, compounds present in the assay sample that may interfere with the observed result, activity of the enzyme, etc.

The substrate compounds of the subject invention have properties that make them more useful than present conventionally used β-galactosidase substrates, e.g., ONPG, in a number of situations. The subject compounds and the products released upon hydrolysis of the subject compounds by β-galactosidase differ from conventional β-galactosidase substrates in several characteristics. The totality of these different characteristics makes the subject compounds more useful than presently availble β-galactosidase substrates.

The subject compounds differ from conventional β-galactosidase substrates by virtue of the absorbance properties of their nitrophenyl derivative reaction products. The molar extinction coefficient of the nitrophenyl derivatives produced by hydrolysis of the subject compounds are, in general, larger than those of the hydrolysis products of conventional β-galactosidase substrates like ONPG. Increasing the molar extinction coefficient ($\epsilon$) of the reaction product makes the assay more sensitive to spectrophotometric detection because for a given concentration, signal strength will be increased. Increased signal strength will be especially desirable when the amount of binding reaction which is modulated is low, for example when sample volume is small, the analyte concentration is low, or when enzymatic activity is low. Increasing the molar extinction coefficient also increases the speed with which the assay can be completed because all things being equal, a detectable signal will be attained more rapidly. The new substrates can thus be employed advantageously in these situations so, as to give rise to more sensitive assays having a lower absorption background.

The substrates in this application have different solubilities from conventional β-galactosidase substrates. The usefulness of this property will be dependent upon the environment in which the assay is performed. Attention should be drawn to the high aqueous solubility of NSPG (see table 1).

The compounds are also found to have good hydrolyric storage stability so that reagent solutions may be prepared and used for extended periods of time. In addition the subject compounds may be prepared from generally available compounds in simple efficient economical chemical processes.

The compounds described in this application are particularly useful with CEDIA™ assays as compared with conventional β-galactosidase substrates.

The following examples are offered by way of illustration and not by way of limitation.

EXAMPLES

Example 1

Synthesis of o-Methoxy-p-nitrophenol Galactopyranoside (NGPG)

MATERIALS

I. o-Methoxy-p-nitrophenol (220 mg, Aldrich)

II. Acetobromo galactose (0.6 g, Sigma)

III. Potassium carbonate (anhydrous) (0.25 g)

IV. Acetonitrile (8 ml)

V. Methanol (50 ml)

VI. 25% Sodium methoxide/methanol reagent (Aldrich)

VII. Acetic acid (0.5 ml)

PROCEDURE

Components I, II, and III were set in a 25 ml flask fitted with a magnetic stirrer. To this mixture was added IV and the resulting mixture stirred at room temperature for 24 hours. The reaction mixture was filtered and the filtrate reduced to a thick glass by rotary evaporation at aspirator pressure (water bath=50° C.).

This glass was reconstituted in 3 ml of acetone and the solution applied to two 20 cm×20 cm silica preparative TLC plates (2000µ thickness, Analtech) containing a short wavelength fluorophore. The plates were dried and developed in chloroform twice. The plates were irradiated with short wavelength UV light and the dark blue band at Rf=0.2–0.3 was marked. This silica gel band was scraped, eluded with acetone, and the acetone removed from the elutant to yield a clear oil.

To this oil was added 7 ml of methanol and the oil slowly dissolved by vigorous stirring. To the resulting solution was added 0.2 ml of VI dropwise and the solution stirred for twenty minutes. The solution was then set on a rotary evaporator with the bath temperature at 60° C. and the solution reduced to about half the volume. The solution was taken off the rotary evaporator and the resulting solution treated with 5 µl aliquots of glacial acetic acid until the addition of 3 µl aliquots of the solution resulted in slightly acidic responses when added to wet pH paper (10 µl of acetic acid were used).

The solution was then reduced to dryness by rotary evaporation and the resulting glass set under vacuum for an hour. The material was then crystallized from 35 ml of methanol to give 140 mg of a white crystalline powder.

Example 2

Synthesis of 5-Nitro-Salicylaldehyde Galactopyranoside (NSPG)

MATERIALS

I. 5-Nitrosalicylaldehyde (300 mg, Aldrich)

II. Acetobromo galactose (0.6 g, Sigma)

III. Potassium carbonate (anhydrous) (0.30 g)

IV. Acetonitrile (8 ml)

V. Methanol (50 ml)

VI. 25% Sodium methoxide/methanol reagent (Aldrich)

VII. Acetic acid (0.5 ml)

PROCEDURE

Components I, II., and III were set in a 25 ml flask, fitted with a magnetic stirrer. To this mixture was added IV and the resulting mixture stirred at room temperature for 24 hours. The reaction mixture was filtered and the filtrate reduced to a thick glass by rotary evaporation at aspirator pressure (water bath=50° C.).

This glass was reconstituted in 3 ml of acetone and the solution applied to two 20 cm×20 cm silica preparative TLC plates (2000µ thickness, Analtech) containing a short wavelength fluorophore. The plates were dried and developed in chloroform twice. The plates were irradiated with short wavelength UV light and the dark blue band at Rf=0.1–0.2 was marked. This silica gel band was scraped, eluted with acetone, and the acetone removed from the elutant to yield a clear oil.

To this oil was added 7 ml of methanol and the oil slowly dissolved by vigorous stirring. To the resulting solution was added 0.2 ml of VI dropwise and the solution stirred for twenty minutes. The solution was then set on a rotary evaporator, at aspirator presure, with the bath temperature 60° C. and the solution reduced to about half the volume. The solution was taken off the rotary evaporator and the resulting solution treated with 5 μl aliquots of glacial acetic acid until the addition of 3 μl aliquots of the solution resulted in slightly acidic responses when added to wet pH paper (15 μl of acetic acid were used).

The solution was then reduced to dryness by rotary evaporation and the resulting glass set under vacuum for an hour. Crystallization from methanol was not sucessful, so the material was treated with 15 ml of distilled water and this solution extracted (3×5 ml) with ethyl ether. The aqueous solution was then set into lyophilization vials, frozen in a −70° C. freezer for two hours, and lyophilized overnight to give a pale yellow fluffy product of approximately 140 mg.

Example 3

Synthesis of 3,4-Dinitrophenol Galactopyranoside (3,4 DNPG)

MATERIALS

I. 3,4-Dinitrophenol (220 mg, Fluka)
II. Acetobromo galactose (0.6 g, Sigma)
III. Potassium carbonate (anhydrous) (0.25 g)
IV. Acetonitrile (8 ml)
V. Methanol (50 ml)
VI. 25% Sodium methoxide/methanol reagent (Aldrich)
VII. Acetic acid (0.5 ml)

PROCEDURE

Components I, II, and III were set in a 25 ml flask fitted with a magnetic stirrer. To this mixture was added IV and the resulting mixture stirred at room temperature for 24 hours. The reaction mixture was filtered and the filtrate reduced to a thick glass by rotary evaporation at aspirator pressure (water bath=50° C.)

This glass was reconstituted in 3 ml of acetone and the solution applied to two 20 cm×20 cm silica preparative TLC plates (2000μ thickness, Analtech) containing a short wavelength fluorophore. The plates were dried and developed in chloroform twice. The plates were irradiated with short wavelength UV light and the dark blue band at Rf=0.2–0.3 was marked. This silica gel band was scraped, eluted with acetone, and the acetone removed from the elutant to yield a clear oil.

To this oil was added 7 ml of methanol containing 0.3 ml of IV and the oil slowly turned into the mixture by vigorous stirring for 20 minutes. A very pale yellow precipitate formed gradually and the mixture allowed to stand for one hour. The mixture was then treated with 5 μl aliquots of glacial acetic acid until addition of 3 μl aliquots of the solution resulted in neutral to slightly acidic responses when added to wet pH paper (10 μl of acetic acid were used). The solid was then filtered off and crystallized from 10–12 ml of methanol to give 190 mg of a white crystalline solid.

Example 4

Synthesis of m-Cyano-p-Nitrophenol

MATERIALS

I. Glacial acetic acid (9.0 ml)
II. Sodium acetate (anhydrous) (1.0 g)
III. Hydroxylamine hydrochloride (0.6 g)
IV. 5-Hydroxy-2-nitrobenzaldehyde

PROCEDURE

A mixture of I and II was set in a 25 ml round bottom flask and set to reflux in an oil bath. A distillation head was set on the flask and a 2 ml volume of distillate collected. At this point, the reaction flask was removed from the oil bath, materials III and IV added to the hot solution, and a reflux condenser substituted for the distillation head. The resulting mixture was set to reflux in the oil bath for three hours, then the reaction flask removed and cooled to ambient temperature over 1.5 hours. During this time, a precipitate had formed and this material was filtered, suction dried for ten minutes, then set in a vacuum oven for an hour to give 450 mg of a yellow solid. The IR spectrum of the material showed a pronounced absorbance at 2250 $cm^{-1}$ in the infrared, indicating the presence of the cyano group, and was identical to that of a product isolated from the nitration of m-cyanophenol.

Example 5

Synthesis of m-Cyano-p-Nitrophenol Galactopyranoside (m—CN—NGP)

MATERIALS

I. m-Cyano-p-Nitrophenol (620 mg, example 4)
II. Acetobromo galactose (1.8 g, Sigma)
III. Potassium carbonate (anhydrous) (0.9 g)
IV. Acetonitrile (18 ml)
V. Methanol (100 ml)
VI. 25% Sodium methoxide/methanol reagent (Aldrich)
VII. Acetic acid (0.5 ml)

PROCEDURE

Components I, II, and III were set in a 50 ml Erlenmeyer flask fitted with a magnetic stirrer. To this mixture was added IV and the resulting mixture stirred at room temperature for 24 hours. The reaction mixture was filtered and the filtrate reduced to a thick glass by rotary evaporation at aspirator pressure (water bath= 50° C.).

To this glass was added 10 ml of methanol and the glass slowly dissolved by vigorous stirring. To the resulting solution was added 0.5 ml of VI dropwise and the solution stirred for twenty minutes. The solution was then set on a rotary evaporator with the bath temperature at 60° C. and the solution reduced to about half the volume. The solution was taken off the rotary evaporator and the resulting solution treated with 5 μl aliquots of glacial acetic acid until the addition of 3 μl aliquots of the solution resulted in slightly acidic responses when added to wet pH paper (40 μl of acetic acid were used).

The solution was then reduced to dryness by rotary evaporation and the resulting glass set under vacuum for one hour. The resulting glass was then crystallized from 60 ml of methanol to give 550 mg of pale yellow material.

Example 6

Characterization of Physical Properties of Substrates

Table 1 gives the the absorbance wavelength maximum ($\lambda_{max}$) for the substrate and the reaction product, the molar extinction coefficient ε for the substrate and the reaction product, the solubility, and the spontaneous hydrolysis rate of the new substrates (stability). ONPG, the standard β-galactosidase substrate, is listed for comparision.

It can be seen that all four subject compounds display a reaction product ε that is 4–6 fold higher than that achieved with ONPG. The high solubility of NSPG should be noted. The high ε and high solubility of NSPG can be used to boost the sensitivity of an assay, since both relative signal strength and the absolute amount of signal can be increased.

TABLE 1

| Substrate | Hydrolysis mA/day* | Solubility mg/ml | Substrate $\lambda_{max}$ (nm) | Substrate ε (OD/M) | Product $\lambda_{max}$ (nm) | Product ε (OD/M) |
|---|---|---|---|---|---|---|
| NSPG | 19 | >40.0 | 298 | 14900 | 382 | 16500 |
| NGPG | 1 | 1.0 | 298 | 7400 | 430 | 17600 |
| m-CN-NPG | 5 | >8.0 | 308 | 9200 | 405 | 17000 |
| 3,4 DNPG | 6 | 3.0 | 280 | 6000 | 400 | 12400 |
| ONPG | 0.4 | 10.0 | 315 | 2000 | 414 | 3000 |

*Hydrolysis is measured at room temperature. Results are normalized to 100 μg/ml starting concentration of substrate.

Example 7

Kinetic Properties of New Substrates

The ability of the subject compounds to act as substrates for β-galactosidase and ED28-digoxgenin+ EA was measured and compared with the results obtained with ONPG. ED28-digoxigenin+ EA are a β-galactosidase α fragment-digoxigenin conjugate and the α complementation acceptor, respectively. ED28-digoxigenin consists of β-galactosidase amino acids 1–46, with cysteines at positions 1 and 46, and digoxgenin conjugated to the cysteines. Assays involving ED and EA are described in greater detail in U.S. Pat. No. 4,708,929. E28-digoxigenin and EA are usually components of a CEDIA™ assay; however, in this set of experiments, antibodies are not present. Four or five substrate concentrations were used to obtain the results. The assay results are given in table 2. The turnover figures are given for EA+ED28-digoxigenin, not β-galactosidase.

Both enzymes clearly display an approximately 3 fold higher Vm when measured with the new subtrates as compared with ONPG. Both enzymes display approximately the same Km for most of the new substrates as they do for ONPG. NGPG appears to exhibit a somewhat lower affinity than ONPG for both enzymes.

TABLE 2

| Substrate | β-galactosidase Km (mg/ml) | β-galactosidase Vm Ratio to ONPG | EA + ED28-digoxgenin Km (mg/ml) | EA + ED28-digoxgenin Vm Ratio to ONPG | Turnover % ONPG |
|---|---|---|---|---|---|
| ONPG | 0.08 | 1.0 | 0.15 | 1.0 | 100 |
| NSPG | 0.11 | 3.2 | 0.14 | 3.0 | 54 |
| 3,4 DNPG | 0.16 | 3.5 | 0.19 | 2.8 | 70 |
| m-CN-NPG | 0.12 | 3.0 | 0.14 | 2.4 | 44 |
| NGPG | 0.24 | 3.7 | 0.28 | 3.6 | 56 |

Example 8

Use of Substrates in CEDIA™ Assays

The ability of the new substrates to function in CEDIA™ assays was tested. The results are given in table 3. All values are relative to reaction rates using OCNPG (o-chloro-nitrophenyl-β-D-galactopyranoside). OCNPG is used as a standard instead of ONPG because ONPG gives an exceptionally weak signal in CEDIA™ assays. CEDIA™ assays for T3 (the thyroid hormone, triiodothyronine), digoxin, and folate were performed.

The terms in table 3 are defined as follows. [Substrate]/Km is the ratio of the concentration of substrate used in the assay to the Km of the enzyme for that substrate. The % open, % inhibition, % mod, and % net figures are all given relative to the results obtained with OCNPG.

% Open is the reaction rate in the absence of antibody. The figure given in table 3 is the reaction rate relative to the reaction rate obtained with OCNPG.

% Inhibition is defined as the difference between the reaction rate rate in the absence of antibody and the reaction rate in the presence of the inhibitory antibody found in the CEDIA™ assays, divided by the reaction rate in the absence of antibody. The figures given in table 3 are relative to the % inhibition figure obtained with OCNPG as substrate.

% Net is defined as the difference between the reaction rate of a CEDIA™ assay using the test substrate in the absence of analyte and presence of antibody and the same reaction in the presence of a saturating amount of analyte (i.e. maximum attainable reaction rate) and presence of antibody, divided by the difference between the reaction rate using OCNPG in the absence of analyte and presence of antibody, and the reaction rate with OCNPG using a saturating amount of analyte and presence of antibody.

% Mod is defined as the difference between the reaction rate of a CEDIA™ assay in the absence of analyte and presence of antibody and the same reaction in the presence of a saturating amount of analyte (i.e., maximum attainable reaction rate) and presence of antibody, divided by the same figure obtained for the reaction rate in the presence of a saturating amount analyte. The greater the % mod, the greater the range of analyte concentrations over which the assay will be effective. The figure given in Table 3 is the mod figure obtained for the new subtrate, divided by % the % mod figure divided % mod figure obtained for OCNPG.

It can be seen in Table 3 that the results obtained with the new compounds are not significantly different from those obtained with OCNPG, although ideally the figures should be 100% or greater than those obtained with OCNPG. It should be noted that the T3 assay results obtained with m—CN—NPG are improved when the concentration of the substrate is increased from 2.7×Km to 4.1×Km.

TABLE 3

| Substrate | [Substrate]/Km | % Open | % Inhib | High calib % Mod | High calib % Net |
|---|---|---|---|---|---|
| Digoxin Assay | | | | | |
| DNPG | 4.0x | 92 | 74 | 85 | 72 |
| m-CN-NP | 4.0x | 82 | 91 | 85 | 71 |
| NGPG | 4.0x | 81 | 98 | 85 | 72 |
| Folate Assay | | | | | |
| DNPG | 3.2x | 72 | 77 | 76 | 58 |
| m-CN-NPG | 2.5x | 62 | 93 | 103 | 72 |
| NGPG | 3.2x | 85 | 104 | 102 | 84 |
| T3 Assay | | | | | |
| DNPG | 3.3x | 73 | 93 | 88 | 71 |
| m-CN-NPG | 4.1x | 71 | 100 | 100 | 63 |
| NGPG | 2.0x | 41 | 87 | 82 | 37 |

It is evident from the preceding discussion and examples that novel compounds are provided which provide numerous advantages for use in detecting β-galactosidase activity in a variety of situations. The compounds offer a number of desirable properties, such as different absorption maxima, enhanced rates in an enzyme medium, which is as a result of solubility, Km and Vmax, ease of synthesis, and high coefficients of extinction.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. In a method for determining the β-galactosidase enzyme activity of a medium, the improvement which comprises:

using as the enzyme substrate a compound for use as a substrate by enzymes with β-galactosidase activity, said compound having the formula:

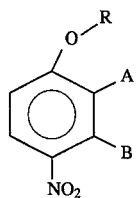

I wherein:

R is β-D-galactosidyl;

A is selected from the group consisting of —OCH$_3$ and —CHO, when B is H;

and

B is selected from the group consisting of —NO$_2$ and —CN, when A is H;

and one of A and B is H.

2. A method according to claim 1, wherein said β-galactosidase activity is as a result of the complexing of a β-galactosidase enzyme donor fragment and enzyme acceptor fragment to form active enzyme.

3. A method according to claim 2, wherein said enzyme donor fragment is conjugated to a compound cross-reactive with an analyte of interest.

4. A method according to claim 1, wherein said β-galactosidase enzyme activity is employed as a label in a heterogenous assay.

5. A method according to claim 4, wherein said heterogenous assay is an ELISA.

6. A method according to claim 4, wherein said assay is for the detection of a nucleotide probe.

* * * * *